(12) United States Patent
Stevens et al.

(10) Patent No.: US 10,309,833 B2
(45) Date of Patent: Jun. 4, 2019

(54) ROOM-TEMPERATURE QUANTUM NOISE LIMITED SPECTROMETRY AND METHODS OF THE SAME

(71) Applicant: Lawrence Livermore National Security, LLC, Livermore, CA (US)

(72) Inventors: Charles G. Stevens, Danville, CA (US); Joseph W. Tringe, Walnut Creek, CA (US); Christopher T. Cunningham, Livermore, CA (US)

(73) Assignee: Lawrence Livermore National Security, LLC, Livermore, CA (US)

( * ) Notice: Subject to any disclaimer, the term of this patent is extended or adjusted under 35 U.S.C. 154(b) by 0 days.

(21) Appl. No.: 15/960,350

(22) Filed: Apr. 23, 2018

(65) Prior Publication Data

US 2018/0245982 A1 Aug. 30, 2018

Related U.S. Application Data

(60) Division of application No. 15/178,444, filed on Jun. 9, 2016, now Pat. No. 9,970,820, which is a continuation of application No. 14/331,193, filed on Jul. 14, 2014, now Pat. No. 9,404,801, which is a continuation of application No. 13/076,162, filed on Mar. 30, 2011, now Pat. No. 8,816,284.

(60) Provisional application No. 61/319,130, filed on Mar. 30, 2010.

(51) Int. Cl.
| | |
|---|---|
| *G01J 3/453* | (2006.01) |
| *G01J 3/433* | (2006.01) |
| *G01J 3/10* | (2006.01) |
| *G01N 21/35* | (2014.01) |

(52) U.S. Cl.
CPC .............. *G01J 3/453* (2013.01); *G01J 3/10* (2013.01); *G01J 3/4338* (2013.01); *G01N 21/35* (2013.01)

(58) Field of Classification Search
CPC ............ G01J 3/453; G01J 3/10; G01J 3/4338; G01N 21/35
USPC ..................................... 250/339.01
See application file for complete search history.

(56) References Cited

U.S. PATENT DOCUMENTS

| | | | | |
|---|---|---|---|---|
| 3,413,468 | A * | 11/1968 | Astheimer | G01J 1/04 250/227.32 |
| 4,491,867 | A * | 1/1985 | Huignard | G01J 9/04 348/164 |
| 5,227,800 | A * | 7/1993 | Huguenin | G01S 7/024 250/332 |
| 5,313,073 | A * | 5/1994 | Kuroda | H01L 31/035236 257/18 |
| 5,452,118 | A * | 9/1995 | Maruska | G02B 6/12004 257/82 |
| 5,545,896 | A * | 8/1996 | Bratt | G01J 5/02 250/338.1 |
| 5,585,953 | A * | 12/1996 | Zavrel | H04B 7/00 340/13.22 |
| 5,751,830 | A * | 5/1998 | Hutchinson | G01S 17/89 382/103 |

(Continued)

*Primary Examiner* — Taeho Jo
(74) *Attorney, Agent, or Firm* — Zilka-Kotab

(57) ABSTRACT

According to one embodiment, a method of forming a plasmonic condensing lens for room temperature quantum noise limited (QNL) infrared (IR) spectrometry includes: forming a silicon cone on a substrate; coating the silicon cone with a highly reflective material; and modifying the silicon cone using focused ion beam (FIB) modification to permit transmittance of light through the silicon cone.

10 Claims, 7 Drawing Sheets

(56) References Cited

U.S. PATENT DOCUMENTS

| | | | | |
|---|---|---|---|---|
| 5,887,009 A * | 3/1999 | Mandella | | B82Y 15/00 372/6 |
| 5,891,738 A * | 4/1999 | Soini | | G01N 33/54313 435/6.11 |
| 6,073,851 A * | 6/2000 | Olmstead | | G06K 7/10702 235/454 |
| 6,111,642 A * | 8/2000 | DeFreez | | G01N 15/0211 250/574 |
| 6,335,522 B1 * | 1/2002 | Shimada | | B82Y 20/00 250/201.3 |
| 7,355,716 B2 * | 4/2008 | de Boer | | A61B 5/0059 356/479 |
| 7,391,564 B2 * | 6/2008 | Komiyama | | G01Q 60/22 359/350 |
| 7,561,813 B2 * | 7/2009 | Jackson | | G01J 9/04 398/204 |
| 7,877,015 B2 * | 1/2011 | Labbe | | G02F 2/002 398/115 |
| 7,948,610 B2 * | 5/2011 | Hintz | | G01S 7/4802 356/4.01 |
| 8,027,094 B2 * | 9/2011 | Day | | B82Y 20/00 359/641 |
| 2003/0099279 A1 * | 5/2003 | Venkatasubramanian | | B82Y 10/00 374/179 |
| 2003/0128634 A1 * | 7/2003 | Challener | | B82Y 20/00 369/13.33 |
| 2004/0142504 A1 * | 7/2004 | Razeghi | | B82Y 20/00 438/93 |
| 2004/0201514 A1 * | 10/2004 | Stappaerts | | G01S 7/486 342/25 R |
| 2005/0152631 A1 * | 7/2005 | Labbe | | G02F 1/0356 385/1 |
| 2005/0202793 A1 * | 9/2005 | Baney | | H04B 10/60 455/189.1 |
| 2006/0054792 A1 * | 3/2006 | Ramer | | G01S 3/781 250/221 |
| 2006/0170925 A1 * | 8/2006 | Lin | | G01N 21/553 356/445 |
| 2007/0257194 A1 * | 11/2007 | Mueller | | G01N 21/3581 250/341.8 |
| 2008/0094613 A1 * | 4/2008 | de Boer | | A61B 5/0059 356/73 |
| 2008/0152349 A1 * | 6/2008 | Weitzel | | G01J 3/453 398/139 |
| 2009/0142016 A1 * | 6/2009 | Aksyuk | | B82Y 20/00 385/14 |
| 2009/0217967 A1 * | 9/2009 | Hovel | | B82Y 20/00 136/249 |
| 2009/0261250 A1 * | 10/2009 | Zhou | | G01B 11/2441 250/307 |
| 2010/0051900 A1 * | 3/2010 | Huffaker | | B82Y 20/00 257/13 |
| 2011/0249546 A1 * | 10/2011 | Choo | | B82Y 20/00 369/112.18 |
| 2012/0025074 A1 * | 2/2012 | Barbi | | G01T 1/2018 250/307 |
| 2012/0038805 A1 * | 2/2012 | Kelly | | G02B 26/0833 348/300 |
| 2012/0182178 A1 * | 7/2012 | Pesetski | | H03D 7/02 342/179 |

* cited by examiner

ROOM-TEMPERATURE QUANTUM NOISE LIMITED SPECTROMETRY AND METHODS OF THE SAME

The United States Government has rights in this invention pursuant to Contract No. DE-AC52-07NA27344 between the United States Department of Energy and Lawrence Livermore National Security, LLC for the operation of Lawrence Livermore National Laboratory.

FIELD OF THE INVENTION

The present invention relates to spectrometry, and more particularly, to quantum noise limited performance in spectrometers.

BACKGROUND

Infrared spectral detection systems are useful in a variety of applications, especially for ground and space based persistent surveillance. Impediments to field deployment of hyper-spectral detection systems include the detector's overall size, weight, and energy usage, which are driven in large part by the requirements of the cooling system for the spectrometer and detector. Therefore, room temperature operation of hyper-spectral detection systems has long been sought to eliminate the vast cooling requirements of conventional hyper-spectral detection systems. However, intrinsic semiconductor detector noise from dark current and radiation from the spectrometer walls presents a significant limitation on system signal-to-noise performance.

One conventional solution to this problem for high-spectral resolution is the use of signal multiplexing, such as Fourier transform spectrometry. This approach detects the entire signal spectral band simultaneously, thereby increasing the competitive position of the signal current with respect to the noise sources. However, even signal multiplexing is overwhelmed by large background flux at elevated temperatures, and at high spectral resolution, this approach fails to achieve quantum noise limited (QNL) performance. QNL performance, where detection sensitivity is limited only by the quantum shot noise of the signal, is a widely used measure with which to determine the performance of signal detection in spectrometry applications.

Another approach uses thermal bolometer detectors for room temperature operation. However, Johnson-Nyquist noise imposes a requirement on these systems for broadband operation, with bandwidths in a range of about 10-90 $cm^{-1}$. In addition, the thermal response times for bolometers impose limits on the operational speed of a spectrometer.

Another approach has been used to achieve QNL performance by heterodyne detection by using a single frequency laser source. In heterodyne detection, a known light source is combined with an incoming signal on a non-linear detector to produce beat frequencies that are amplified and detected. If the known light source generates more detector signal than the sources of noise, a QNL results. Heterodyne detection has historically depended on sufficiently bright light sources provided by narrow beam lasers. These heterodyne approaches rely on tuning the narrow band laser over the spectral region of interest. This tuning of the laser over the spectral band of interest can considerably reduce the efficiency in gathering spectral information over an extended spectral region, however. Conventional incandescent light sources, while potentially bright enough, are extremely inefficient since a substantial fraction of their output is outside the spectral range of interest.

Another approach illustrated in the prior art is to use an immersion condensing lens to reduce the size of the detector. Because dark current is proportional to detector size, this discriminates against background and dark current. A factor of 16 in focal area reduction has been achieved by VIGO for HgCdTe detectors in the long-wave region through the use of high index immersion lens technology. However this reduction is not enough to overcome dark currents sufficiently to allow QNL performance.

Therefore, all these approaches have failed to overcome the imposed limitations on size, weight, and energy usage imposed by cooling requirements. Even if QNL performance is achievable with hyper-spectral detection systems at elevated temperatures, the size, weight, and energy usage limitations placed on implementation of these devices makes their use impractical. Therefore, a hyper-spectral detection system which could reach QNL performance while achieving practical implementation regarding size, weight, and energy usage would be very beneficial, particularly in military and law enforcement efforts to deploy highly sensitive instruments capable of ground-based persistent surveillance and micro-power space surveillance.

SUMMARY

According to another embodiment, a method of forming a plasmonic condensing lens for room temperature quantum noise limited (QNL) infrared (IR) spectrometry includes: forming a silicon cone on a substrate; coating the silicon cone with a highly reflective material; and modifying the silicon cone using focused ion beam (FIB) modification to permit transmittance of light through the silicon cone.

Other aspects and embodiments of the present invention will become apparent from the following detailed description, which, when taken in conjunction with the drawings, illustrate by way of example the principles of the invention.

DETAILED DESCRIPTION

Figure 1:
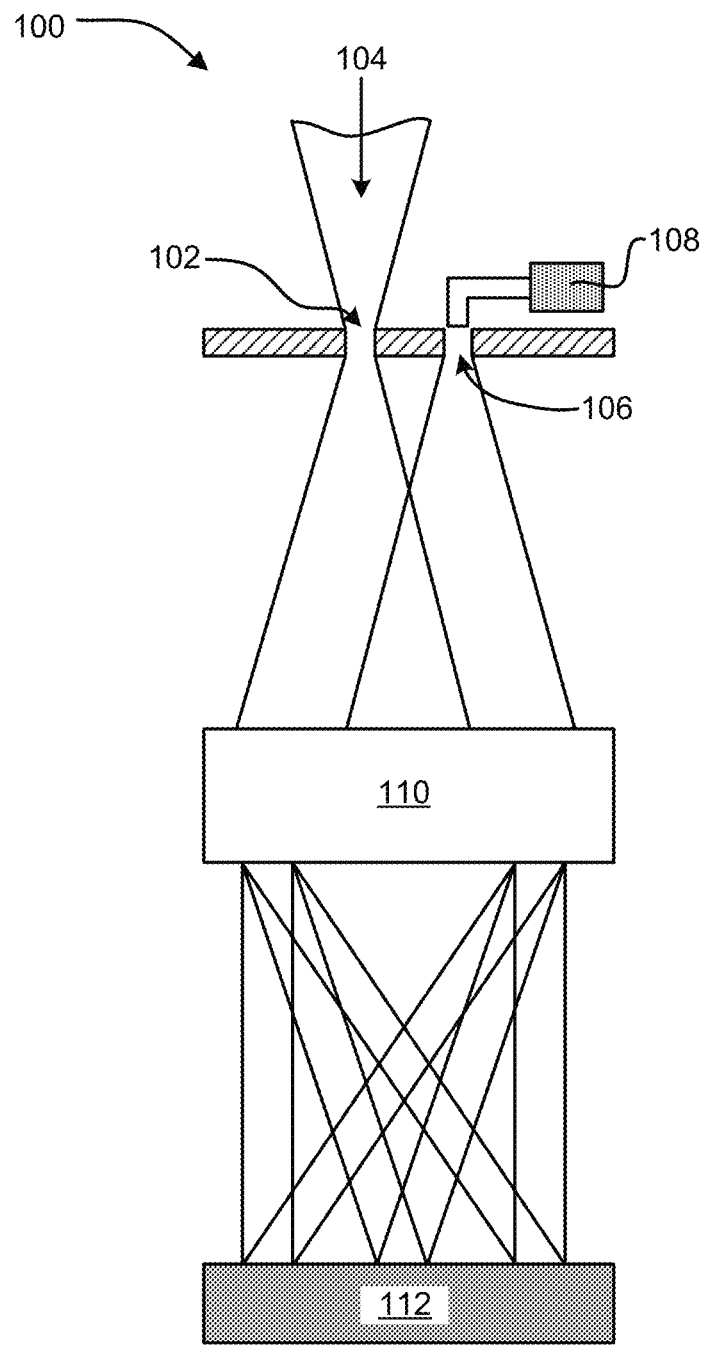
FIG. 1 shows a schematic of a heterodyne spectrometer, according to one embodiment.

The following description is made for the purpose of illustrating the general principles of the present invention and is not meant to limit the inventive concepts claimed herein. Further, particular features described herein can be used in combination with other described features in each of the various possible combinations and permutations.

Unless otherwise specifically defined herein, all terms are to be given their broadest possible interpretation including meanings implied from the specification as well as meanings understood by those skilled in the art and/or as defined in dictionaries, treatises, etc.

It must also be noted that, as used in the specification and the appended claims, the singular forms "a," "an" and "the" include plural referents unless otherwise specified.

In one general embodiment, a heterodyne detection system for detecting light includes a first input aperture adapted for receiving first light from a scene input, a second input aperture adapted for receiving second light from a local oscillator input, a broadband local oscillator adapted for providing the second light to the second input aperture, a dispersive element adapted for dispersing the first light and the second light, and a final condensing lens coupled to an infrared detector. The final condensing lens is adapted for concentrating incident light from a primary condensing lens onto the infrared detector, and the infrared detector is a square-law detector capable of sensing the frequency difference between the first light and the second light.

In another general embodiment, a method for detecting light includes receiving first light from a desired scene in a first input aperture, introducing second light produced by a broadband local oscillator to a second input aperture, passing the first light from the desired scene and the second light produced by the broadband local oscillator through a dispersive element, concentrating the light from the dispersive element onto a detector pixel using a condensing lens coupled to the infrared detector, and detecting simultaneously the first light and the second light using the infrared detector.

According to one embodiment, broadband infrared spectrometry based on the principle of heterodyne detection that improves spectral light gathering efficiency while maintaining sensitivity may be achieved. To accomplish this, light from a broadband local oscillator source, such as a broadband quantum cascade laser or photonic bandgap light source, may be introduced into a dispersive spectrometer at an entrance aperture (window) that is physically or spatially displaced from an input aperture (window) for receiving the desired scene light. The physical displacement between signal and local oscillator translates, after dispersion, into a physical displacement of their spectra on a square-law detector array. Consequently, each pixel of the array responds to two frequencies creating an intermediate beat frequency in the detector output. In this way, hundreds of individual spectral channels may simultaneously record a high resolution infrared spectrum, substantially improving the throughput of heterodyne spectrometry. Additionally, this approach allows for operation at a significantly higher detector temperature than conventional broadband spectrometers.

A broadband heterodyne approach with emerging bright light sources is promising for facilitating low-noise, elevated-temperature infrared detection. One advantage of using a heterodyne detection approach with a bright light source sufficiently powerful for use in hyper-spectral detection systems is evident from the signal-to-noise expression for heterodyne detection, presented below as Equation 1.

$$S/N = (N_s^{1/2} N_{LO}^{1/2}) / [(N_s + N_{LO} + N_{spec} + N_{dark} + N_{other})^{1/2}] \quad \text{(Eq. 1)}$$

In Equation 1, $N_s$, $N_{LO}$, $N_{spec}$ $N_{dark}$ are net signal, local oscillator, spectrometer wall, and dark current photoelectrons, respectively, as collected over the data integration time. This expression exhibits achieving quantum noise limit (QNL) performance when the photoelectrons from the local oscillator exceed other noise sources. $N_{LO}$ then dominates the denominator and cancels itself in the numerator. The expression predicts that elevated-temperature QNL performance is achievable with efficient and bright broadband light sources. This is especially important in the infrared spectral region.

Now referring to FIG. 1, one embodiment of a spectrometer 100 utilizing heterodyne detection is shown, where an input window or aperture 102 for the scene input 104 (source of light to be detected) may be spatially/physically displaced with respect to the input aperture 106 for a bright local broadband oscillator 108. A dispersive element 110, such as a grating, may be used to disperse the signals from the scene input 104 and the bright local broadband oscillator 108 such that the signals are dispersed according to wavelengths. This physical displacement between signal and local oscillator translates, after dispersion, into shifts in the wavelength in the focal plane of the spectrometer 100, e.g., a physical displacement of their spectra. Consequently, each pixel of the array responds to two frequencies creating an intermediate beat frequency in the detector output. An infrared detector 112 registers the displacement shifts in the wavelength. The detector 112 may be an array of photodetectors as known in the relevant art, according to one embodiment, and more preferably is a square-law detector capable of sensing a frequency difference between the light from the aperture 102 and the light from the bright local broadband oscillator 108. The photodetectors may be mixing elements of a type known in the art.

In one approach, where the two frequencies meet spatial and spectral coherency requirements, they coincide at each detector pixel and combine to create a beat frequency with a bandwidth determined by the spectral resolution of the spectrometer 100.

According to various approaches, either, neither, or both apertures 102, 104 may have a lens placed therein for affecting light from the respective input. The lens may be for light shaping, filtering, focusing, concentrating, condensing, etc., and may be of any type known in the art.

In a preferred embodiment, the optical configuration meets an antenna theorem condition such that the product of the aperture area and the collection solid angle is approximately equal to the square of the light source wavelength. Furthermore, spectral coherency is established by the bandwidth of the light intercepted by each pixel, ranging from about 3.0 GHz for a 0.1 cm$^{-1}$ spectrometer to about 30 GHz for a 1.0 cm$^{-1}$ spectrometer. Also, the physical displacement at the entrance may preferably be at least twice the spectral bandwidth, in some approaches.

Recently, the development of photonic bandgap light sources and broadband quantum cascade laser light sources makes it practical to consider using broadband light sources in the spectrometer configuration shown in FIG. 1. Sources that emit light in an adjustable band centered on the wavelength region of interest can be bright and efficient. Commercial photonic bandgap (PBG) sources are equivalent to 1000 K blackbodies in bands of several hundred wavenumbers, from at least about 500 cm$^{-1}$ to about 5000 cm$^{-1}$. Some virtues of the photonic crystal emitters include targeted spectral ranges and output efficiencies at about 5%. The intensity of these sources is sufficient to outpace spectrometer wall flux at ambient temperature for operation at wavelengths shorter than 5 microns. This relaxes the requirement for cooling the entire spectrometer and requires only detector cooling. The intensities of wall radiation and coherent PBG sources are presented in FIG. 2A. This shows that the PBG source has sufficient intensity to serve as a LO for a room temperature spectrometer in the mid-infrared region.

The above analysis assumes that IR detectors have high frequency operation and sufficiently low dark current noise. Recent developments in band-structure engineered materials such as quantum well infrared photodetectors (QWIPs) have the requisite operating frequencies, up to 75 Ghz, but they have high dark currents that require operation at cryogenic temperatures. More recently, new options have opened up in "quantum engineering" of materials, particularly with the development of quantum dot detectors, quantum dot IR photodetectors (QDIPs), and atomic clusters including "metallic semiconductors," that are opening up whole new vistas for searching for combinations of high speed and low dark currents. Limiting the location and density of states inhibits one of the major sources of dark current, Auger processes. Quantum clusters that assign angular momentum to electron trajectories further restrict the electron coupling options by conservation rules.

Figure 2A:
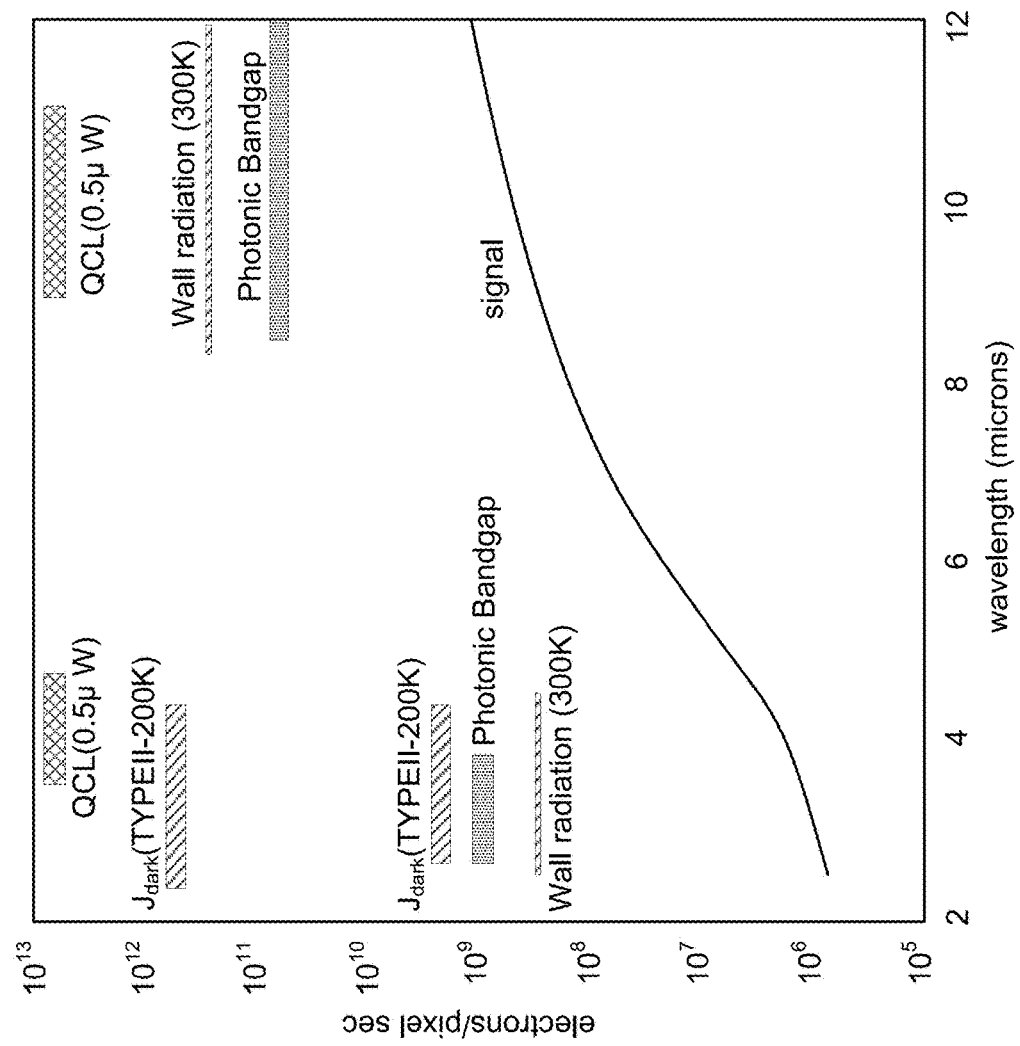
FIG. 2A shows a plot of current (electrons/(pixel sec)) versus wavelength (microns) expected from various sources, according to one embodiment.

Developments along these lines are being pursued with Type II InAs/GaSb superlattice structures. The dark current of these detector types can be significantly lower than that of QWIPs. One example is shown in FIG. 2A for both 200K operation and 300K operation. While the PBG source is bright enough to operate the spectrometer at ambient temperature, a brighter source is needed to overcome detector current.

The development of broadband quantum cascade infrared lasers, offers a potential robust local oscillator option to implement this approach. A 4μ to 5μ cw laser operating at 285K with 1 Watt output and 5% wall plug efficiency has been described. The 400 $cm^{-1}$ span provides about 2.5 mWatts per $cm^{-1}$ wave-number interval. This meets the local oscillator requirement by a wide margin over the detector dark current at ambient temperature. Lowering the overall power consumption to 1 Watt yields about $2 \times 10^{15}$ photons/pixel-sec, more than 2000 times higher than detector dark current. This allows for more than 200 spatial pixels creating the opportunity for an imaging spectrometer. Adjusting the well width of the QCL may provide a LO in the more important 3 to 4 micron spectral region. Comparable QCL sources in the long-wave infrared region provide sufficient power to allow room temperature spectrometer operation. However, detector dark current in this spectral region is currently much too high to operate using uncooled detectors.

Figure 2B:
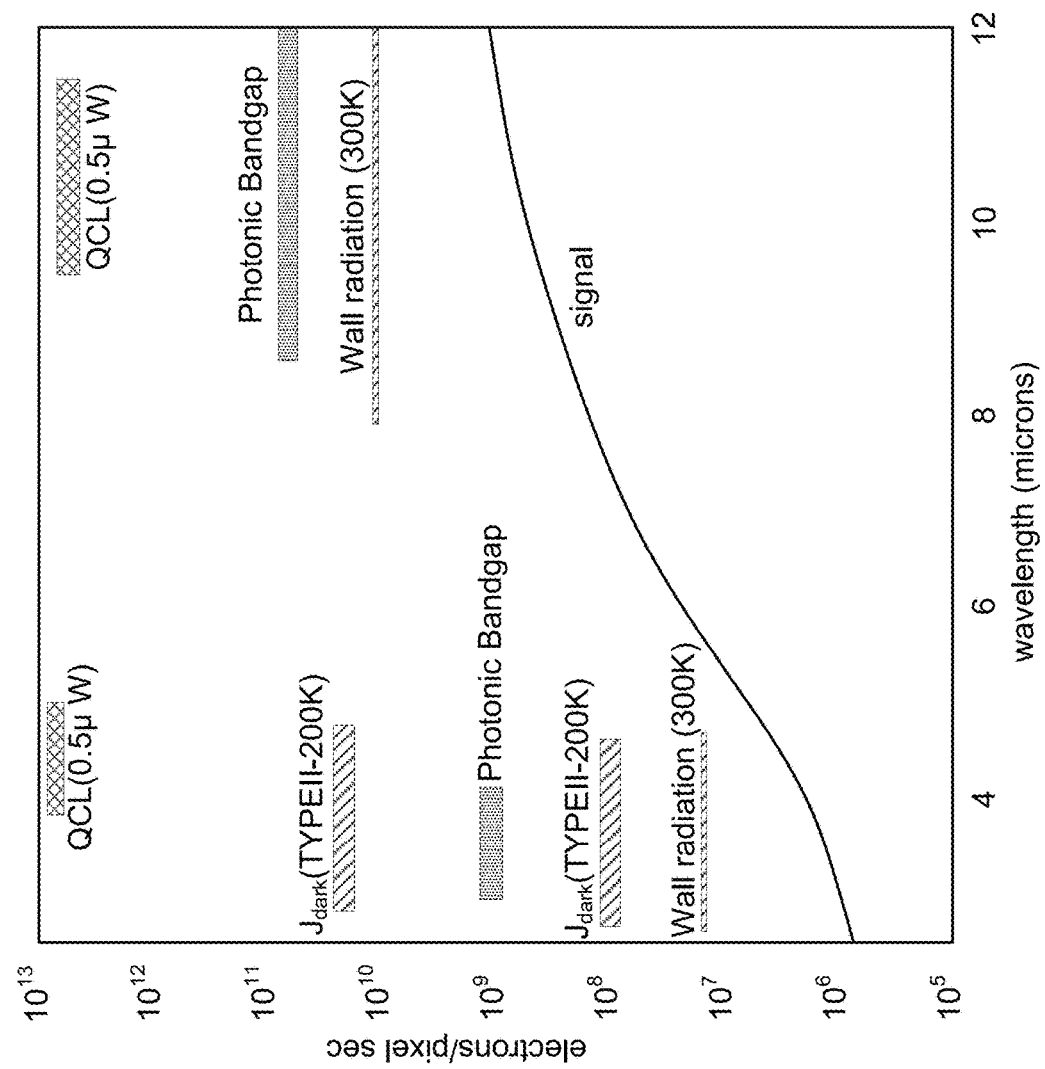
FIG. 2B shows a plot of current (electrons/(pixel sec)) versus wavelength (microns) expected from various sources, according to one embodiment using a condensing superlens.

FIG. 2B illustrates the relative currents for signal, noise sources, and local oscillators expected with the addition of a plasmonic condensing lens (see below) that reduces the detector volume. This reduction directly translates into lower background radiation and lower detector dark current. Using a photonic bandgap broadband source as a local oscillator, a room temperature spectrometer coupled with a detector cooled to 200K is possible. In the long-wave infrared, a room temperature spectrometer with a cryo-cooled detector is possible. In the mid-infrared shorter than 5 microns, the combination of a QLC coupled with a plasmonic condensing lens makes possible QNL operation with a room temperature spectrometer and uncooled detector.

According to one exemplary embodiment, a spectrometer includes a detector, two entrance apertures, and a dispersive element. It may have a resolution of about 1 $cm^{-1}$ that may provide about a 30 GHz band pass system. The two entrance apertures may have a spatial separation of about 30 microns that translates into an overlap of two colors separated by about 30GHz at the detector. This matches a frequency response of fast quantum well detectors (about 32 GHz) that are available. These detectors may be fabricated as single elements or arrays exceeding 250×250 pixels and are multiquantum well structures of composition InAs (9)/GaAs (10) with a lattice period of 58 A. Custom design filter/amplifier following circuits may be included, such as a single detector element with external signal processing or an array with on-board pixel circuit elements. Of course, this is just one exemplary embodiment, and many other approaches may be used in designing dimensions and materials of construction for a spectrometer according to various embodiments.

A spectrometer, according to any embodiment described herein, may include diagnostic/performance measuring and analysis capability, either on-board or accessible through an interface with an external device. To assess the performance of broadband spectrometer designs, a model may be developed that includes key physics elements as comparative values. Inputs to the model may include spatial and temporal characteristics of the broadband source and the signal, filter function, spectral dispersion, spatial (frequency) offset of the local oscillator and signal light, and general detector characteristics, such as efficiency, bandwidth, dark current, etc. The model may be embodied as computer readable code, which may be capable of calculating the heterodyne efficiency due to matching of the local oscillator and signal field distributions at each pixel, the base band detector photocurrent in the presence of Poisson shot noise, detector dark current, wall radiation, and other noise sources (as would be apparent to one of skill in the relevant art), and ultimately the signal-to-noise ratio as a function of the fundamental inputs. Performance may be assessed versus a filter spectral bandwidth and shape, as well as the heterodyne offset (intermediate frequency).

Additionally, a model may be produced to predict the improvement expected from using immersion lenses to focus light onto each pixel. The performance model may leverage a time-domain heterodyne detection code for vibrometry applications, to which may be added the finite local oscillator bandwidth associated with the filtered broadband source.

Figure 3:
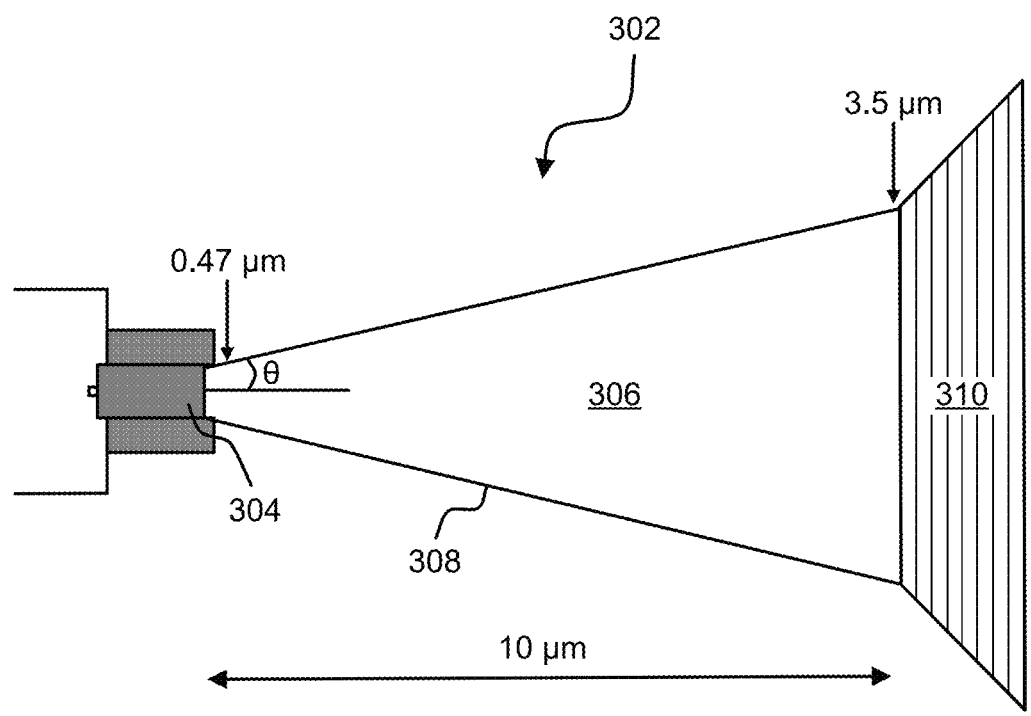
FIG. 3 shows a schematic of a system including a condensing superlens capable of condensing electromagnetic radiation in a cavity mode, according to one embodiment.

Now referring to FIG. 3, in another embodiment, heterodyne detection may be further improved by placing a condensing superlens or immersion micro-lens 302 in contact with detector pixels 304 such that the superlens 302 receives the scene input 310 and condenses the light, thereby increasing the signal-to-noise ratio (SNR) by a factor of $n^2$, where n is the refractive index of the detector pixels 304 (n can be as large as four). In some embodiments, the superlens 302 may increase the SNR and allow QNL in the long-wave infrared range.

In yet another embodiment, a condensing superlens 302 may be used to reduce dark current ($N_{dark}$ in Equation 1), which results from detection events in the complete absence of any light source.

In a preferred embodiment, the condensing superlens 302 may be fabricated from silicon (Si) by reactive ion etching, but any formation technique may be used with any material suitable for transmission of an input signal in a desired wavelength through a superlens. According to one embodiment, fields of Si cones 306 may be formed on $SiO_2$ and coated with highly reflective metal 308 as known in the art, such as gold, copper, silver, platinum, any combination thereof, etc. After coating the Si cone 306 with the reflective metal 308, properly formed cones 306 may be selected for focused ion beam (FIB) modification in order to permit transmittance of light therethrough. In a preferred embodiment, the FIB modification may produce a superlens 302 with an aperture diameter approximately one-seventh (⅐) that of the wavelength of light that is to be detected by the detector pixels 304. Furthermore, preferred embodiments may place the superlens 302 in direct contact with the detector pixels 304 to improve light absorption therein.

Some exemplary dimensions are indicated in FIG. 3, with a length of the superlens being about 10 μm, a diameter at a receiving end being about 3.5 μm, and a diameter at a transmitting end being about 0.47 μm. Of course, any dimensions may be used, as would be apparent to one of skill in the art, particularly when taking into account a SNR increase desired, a size of individual pixels in the photodetector, the material used, the wavelength of light to be detected, etc.

General derivatives of the preferred embodiment of the condensing superlens 302 may be fabricated from any material known in the art, with the only requirement being that the material be transparent to the wavelength of light to be detected. For example, IR light is transmittable through Si, which makes Si a possible material for a superlens used to condense IR light for detection.

An electromagnetic wave can propagate in a conical cavity until the diameter of the cavity approaches one-half wavelength of light in the propagating medium. The focal spot of a lens would be substantially larger, by twice the F-number, for a wave in a perfectly conducting cavity.

This discussion is based on treatment of cylindrical waveguides and fibers, which extends to a conical geometry. If the field cannot be free of an axial component, the coefficient of this component satisfies a wave-like equation, and from it the remainder of the field can be determined. The resulting solutions can be expressed analytically in terms of Bessel functions. Electric and magnetic fields are assumed to have the time dependence $\varepsilon = Ee^{-i\omega t}$ and $\beta = Be^{-i\omega t}$, respectively.

Maxwell's equations in a uniform nondissipative medium of permittivity $\varepsilon$, permeability $\mu$, wave number $k = (\mu\varepsilon)^{1/2}\omega$ are shown below in Equation 8.

$$\nabla \times E = i\omega B \quad \nabla \cdot E = 0 \quad \nabla \times B = (k^2/i\omega)E \quad \nabla \cdot B = 0 \tag{Eq. 8}$$

However, because of the similarity of the E and B fields, $\Psi$ may represent either value, thus:

$$\nabla \times \nabla \times \Psi = k^2 \Psi \tag{Eq. 9a}$$

$$\nabla \cdot \Psi = 0 \tag{Eq. 9b}$$

In spherical coordinates $(r, \theta, \phi)$ orthonormal unit vectors $\{e_1, e_2, e_3\}$ are used in the $\{r, \theta, \phi\}$ directions, for which $\Psi = e_1\Psi_1 + e_2\Psi_2 + e_3\Psi_3$, which is referred to as $\{$"radial," "axial," "circular,"$\}$, respectively. Similarly, "transverse" means non-radial on the $e_2, e_3$ surface. With $s = \sin(\theta)$, $$\nabla \cdot \Psi = (1/r^2)(r^2\Psi_1)_{,r} + (1/rs)(s\Psi_2)_{,\theta} + (1/rs)\Psi_{3,\phi} = 0 \tag{Eq. 10a}$$

$$\nabla \times \Psi = (e_1/rs)[(s\Psi_3)_{,\theta} - \Psi_{2,\phi}] + (e_2/rs)[\Psi_{1,\phi} - (rs\Psi_3)_{,r}] + (e_3/r)[(r\Psi_2)_{,r} - \Psi_{1,\theta}] \tag{Eq. 10b}$$

Thus, according to Equation 10a which allows $\Psi_2$ and $\Psi_3$ to be replaced with $\Psi_1$, the wave equation for $\Psi_1$ is:

$$(1/r^2)[(r^2\psi_1)_{,rr} + (1/s)(s\psi_{1,\theta})_{,\theta} + (1/s^2)\psi_{1,\phi\phi}] + k^2\psi_1 = 0 \tag{Eq. 11}$$

Next a separable solution is sought to the wave Equation 11 having the form:

$$\psi_1 \propto R_1(r)\Theta_1(\theta)\Phi_1(\phi) \tag{Eq. 12}$$

This leads to the following eigenvalue equations:

$$(r^2 R_1)_{,rr} + (k^2 r^2 - l(l+1))R_1 = 0 \tag{Eq. 13c}$$

$$(1/s)(s\Theta_{1,\theta})_{,\theta} + (l(l+1) - m^2/s^2)\Theta_1 = 0 \tag{Eq. 13b}$$

$$\Phi_{1,\phi\phi} + m^2\Phi_1 \tag{Eq. 13a}$$

Substituting $x = kr$, $X = x^{3/2}R_1$, or $R_1 = x^{-3/2}X$ into Equation 13a yields Bessel's equation:

$$x^2 X_{,xx} + x X_{,x} + (x^2 - l(l+1) - 1/4)X = 0 \tag{Eq. 14}$$

However, the large value of l in present applications renders the ¼ term negligible, and solutions are the Bessel and Hankel functions, and with $\upsilon = [l(l+1)]^{1/2}$, the functions have asymptotic forms as x approaches infinity:

$$X_\upsilon(x) = J_\upsilon(x) \to (2/\pi x)^{1/2} \cos(x - 1/2\pi\upsilon - 1/4\pi) \quad \upsilon^2 = l(l+1) \tag{Eq. 15a}$$

$$= Y_\upsilon(x) \to (2/\pi x)^{1/2} \sin(x - 1/2\pi\upsilon - 1/4\pi)$$

$$= H_\upsilon^{(1)}(x) = J_\upsilon(x) + iY_\upsilon(x) \to (2/\pi x)^{1/2} e^{i(x - 1/2\pi\upsilon - 1/4\pi)}$$

$$= H_\upsilon^{(2)}(x) = J_\upsilon(x) - iY_\upsilon(x) \to (2/\pi x)^{1/2} e^{-i(x - 1/2\pi\upsilon - 1/4\pi)}$$

Wherein the functions are related by the expression:

$$X'_\upsilon = X_{\upsilon-1} - (\upsilon/x)X_\upsilon \tag{Eq. 15b}$$

With the implicit $e^{-i\omega t}$ time dependence, the Hankel functions $H^{(1)}$, $H^{(2)}$, represent outgoing, ingoing traveling waves, respectively, and the Bessel functions represent standing waves with equal components of outgoing and ingoing waves.

Since $Y_\upsilon$ and the Hankel functions diverge at small radii, they cannot be physical solutions to the propagation into an empty loss-free cavity because "loss-free" implies perfect reflection. The Bessel function of the first kind, however, corresponds to a well-behaved standing wave with perfect reflection; so, in a loss-free cavity that reaches a sufficiently small diameter $X_\upsilon = J_\upsilon$.

The solutions to Equation 13b are the Legendre polynomials (m=0) and associated Legendre functions $(m \neq 0)^\upsilon$. The solutions to Equation 13c are trigonometry functions.

$$\Theta_1 = P_l^m(c) \quad c = \sin\theta \tag{Eq. 16a}$$

$$\Phi_1 = \{\cos(m\phi), \sin(m\phi)\} \tag{Eq. 16b}$$

Hence, $\psi_1$ is composed of:

$$(\psi_1)_{lm} = \psi_{1lm}\{x^{-3/2}X_\upsilon(x)\}\{P_l^m(c)\}\{\cos(m\phi), \sin(m\phi)\}; \tag{Eq. 17}$$

$\psi_{1lm}$ is a constant.

By analogy, in a waveguide, distinguish modes with transverse electric "TE" fields ($E_1 = 0$) and transverse magnetic "TM" fields ($M_1 = 0$). By this construction, $\Psi_1 \neq 0$, so $\Psi$ is the "non-transverse" field, and $\nabla \times \Psi$ is the "transverse" field.

This choice of modes allows construction of the transverse component of $\Psi$.

$$(\nabla \times \Psi)_1 = (1/rs)[(s\psi_\phi)_{,\theta} - \psi_{\theta,\phi}] = 0 \tag{Eq. 18}$$

Which will be satisfied for a scalar field $\xi$ with:

$$\psi_2 = \xi_{,\theta}, \quad \psi_3 = (1/s)\xi_{,\phi} \tag{Eq. 19}$$

$\nabla \cdot \Psi = 0$ implies $$(1/s)(s\xi_{,\theta})_{,\theta} + 1/s^2)\xi_{,\phi\phi} = -(1/r)(r^2\psi_1)_{,r} \tag{Eq. 20}$$

For a separable solution $\xi = \xi_{lm} R_\xi(r)\Theta_{,\xi}(\theta)\Phi_\xi(\phi)$ $$\xi_{lm} = \psi_{1lm}/l(l+1) \tag{Eq. 21a}$$

$$R_\xi = (x^2 R_1)_{,x}/x \tag{Eq. 21b}$$

$$\Theta_\xi = \Theta_1, \quad \Phi_\xi = \Phi_1 \tag{Eq. 21c}$$

Thus, the entire field for an eigenmode is $$(\psi_1)_{lm} = l(l+1)\xi_{lm} R_1 \{P_l^m(c)\}\{\cos(m\phi), \sin(m\phi)\}$$

$$(\psi_2)_{lm} = \xi_{,\theta} = \xi_{lm} R_\xi \{P_l^m(c)_{,\theta}\}\{\cos(m\phi), \sin(m\phi)\}$$

$(\psi_3)_{lm} = \xi_{,\psi}/s = \xi_{lm} R_{\S}\{P_l^m(c)/s\} \{-\sin(m\phi), \cos(m\phi)\}$ $(\nabla \times \psi)_{1lm} = 0$ (Eq. 22d)

$(\nabla \times \Psi)_{2lm} = (1/rs)[\psi_{1,\phi} - (rs\psi_3)_{,r}] = \xi_{lm} \{kxR_1\} \{mP_l^m(c)/s\} \{-\sin(m\phi), \cos(m\phi)\}$ (Eq. 22e)

$(\nabla \times \Psi)_{3lm} = (1/r)[(r\psi_2) - \psi_{1,\theta}] = \xi_{lm} \{kxR_1\} \{P_l^m(c)_{,\theta}\} \{-\cos(m\phi), -\sin(m\phi)\}$ (Eq. 22f)

$R_1 = x^{-3/2} X_\upsilon(x)$ $R_{\S} = (x^2 R_1)_{,x}/x = x^{-1/2} X_{\upsilon-1}(x) - (\upsilon - \frac{1}{2})R_1$ $P_l^m(c)_{,\theta} = (l+m)(l-m+1)P_l^{m-1}(c) - (mc/s)P_l^m(c)$ (*)

The fields satisfy boundary conditions appropriate for a conductor at the surface of the cone, $\theta = \theta_0$:

$E_1(\theta_0) = E_3(\theta_0) = 0; \ B_2(\theta_0) = 0$ (Eq. 23)

Which is satisfied where $P_l^m(\cos \theta_0) = 0 \ (TM); \ P_l^m(\cos \theta_0)_{,\theta} = 0 \ (TE)$ (Eq. 24)

For a narrow cone with $\theta_0 \ll 1$, $l$ will be large. In this case, $P_l^m(\cos \theta_0) = l^m J_m(l\theta)$ (Eq. 25)

However, (Equation 13b) may be approximated using $s = \sin \theta \approx \theta$ $\alpha^2 P_{l\ ,\alpha\alpha}^m + \alpha P_{l\ ,\theta}^m + (y^2 - m^2)P_l^m \approx 0 \ y = \upsilon\theta \ \upsilon^2 = l(l+1)$ (Eq. 26)

Which yields a more accurate approximation in the form of Bessel's equation:

$P_l^m(c) \approx \upsilon^m J_m(y)$ $m \, P_l^m(c)/s \approx \upsilon^{m+1} m J_m(y)/y$ $P_l^m(c)_{,\theta} \approx \upsilon^{m+1} m J'_m(y) = \upsilon^{m+1}[J_{m-1}(y) - mJ_m(y)/y]$ (Eq. 27a)

In this small $\theta$ approximation, for TE $E_1 = 0$ $E_2 = E \, xR_1 \, mJ_m(y)/y \, \{-\sin(m\phi), \cos(m\phi)\}$ $E_3 = E \, xR_1 \, J'_m(y) \, \{-\cos(m\phi), -\sin(m\phi)\}$ $B_1 = B \, \upsilon R_1 \, J_m(y) \, \{\cos(m\phi), \sin(m\phi)\}$ $B_2 = B \, R_{\S} \, J'_m(y) \, \{\cos(m\phi), \sin(m\phi)\}$ $B_3 = B \, R_{\S} \, mJ_m(y)/y \, \{-\sin(m\phi), \cos(m\phi)\}$ (Eq. 27b)

$R_1 = x^{-3/2} X_\upsilon(x)$ $R_{\S} = (x^2 R_1)_{,x}/x = x^{-1/2} X_{\upsilon-1}(x) - (\upsilon - \frac{1}{2})R_1$ $B = \upsilon^{m+1} \xi_{lm} \, E = (i\omega/k)B$ For TM, B replaces E in Equation 27b, and the eigenvalue $\upsilon^2 = l(l+1)$ satisfies the boundary conditions at $\theta_0$:

$\upsilon_{nm} = y_{nm}/\theta_0$ (Eq. 28)

where $y_{nm}$ is the $n^{th}$ zero of $J'_m$ (TE) or $J_m$ (TM). This simple relation between $\upsilon$ and $\theta_0$ motivates application of the small-angle limit.

TABLE 1

| The Zeroes of $J_m'$ and $J_m$ | | | |
|---|---|---|---|
| $y_{nm}$ (TE) | | | |
| n/m | 0 | 1 | 2 |
| 0 | 3.832 | 1.841 | 3.054 |
| 1 | 7.016 | 5.331 | 6.076 |
| 2 | 10.173 | 8.536 | 9.969 |
| $y_{nm}$ (TB) | | | |
| n/m | 0 | 1 | 2 |
| 0 | 2.045 | 3.832 | 5.136 |
| 1 | 5.520 | 7.016 | 8.417 |
| 2 | 8.864 | 10.173 | 11.620 |

Figure 4:
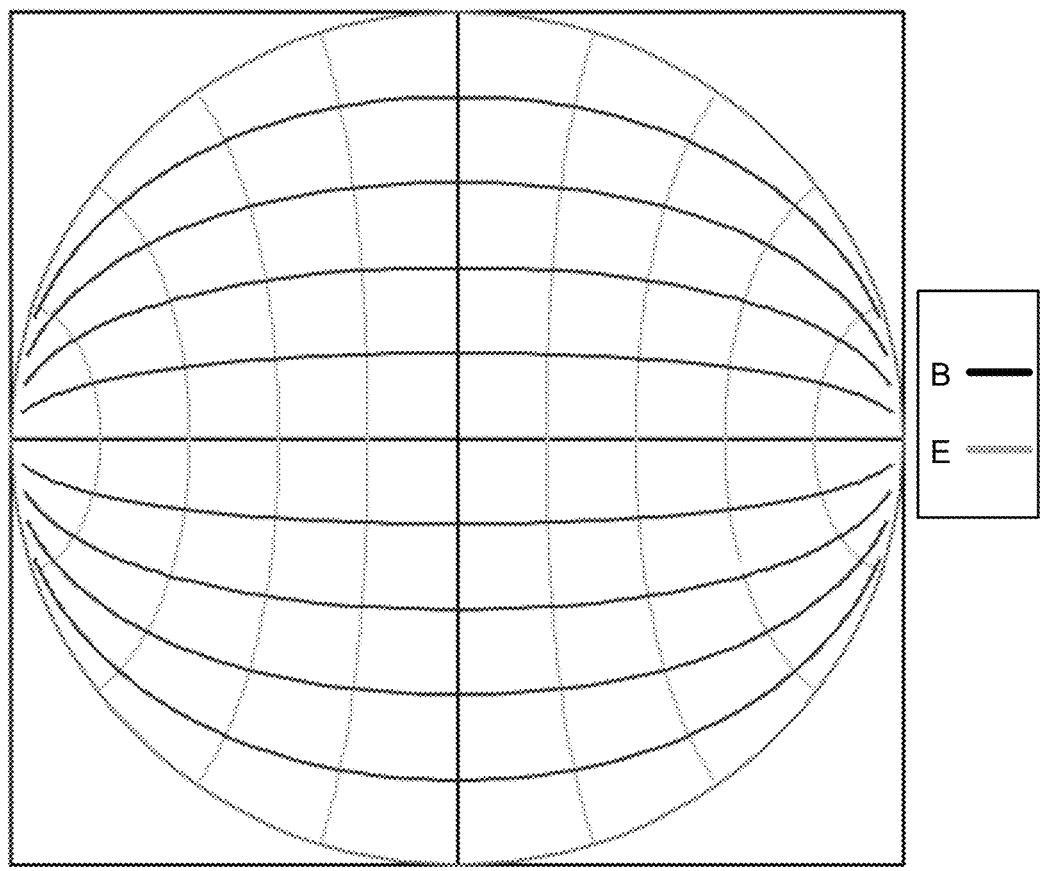
FIG. 4 shows a plot of streamlines for a cavity mode that propagates to the smallest radii, according to one embodiment.

In one embodiment, the mode $TE_{11}$, for which $\upsilon = 1.842/\theta_0$, and $TM_{10}$, for which $\upsilon = 2.405/\theta_0$, since such modes propagate to the smallest radii. Where the cavity is driven by a linearly polarized external field, only the m=1 mode(s) will be excited. Streamlines for the lowest mode TE01 will overlap with the external field and comprises the cavity mode that propagates to the smallest radii, as depicted in FIG. 4. As an indicator of propagation into the cavity, use the energy density in the electromagnetic field. The volume energy density is:

$u = \frac{1}{2}(\epsilon|E|^2 + |B|^2/\mu)$ (Eq. 29)

Wherein the linear density may be expressed by:

$dU/dr = r^2 \int d\theta \, \sin\theta \int d\phi \, u \approx (x/k\upsilon)^2 \int dy \, u \int d\phi \, u$ (Eq. 30)

From Equation 20, the density component for single modes may be evaluated as:

$dU/dR \approx u^*/(\upsilon k)^2 \{2\pi : m=0, \pi : m \neq 0\} I_{nm}(2/\pi) \mathcal{R}\upsilon_\upsilon(x)$ (Eq. 31a)

$u^* = \frac{1}{2}\xi E^2 = \frac{1}{2}B^2/\mu$ (Eq. 31b)

$I_{nm} = \int^{y_{nm}} [J'^2_m + (mJ_m/y)^2] y \, dy$ (Eq. 31c)

$\mathcal{R}\upsilon_\upsilon(x) = (\pi/2)[(x^2 + f\upsilon^2)|xR_1|^2 + x^2|R_{\S}|^2]$ (Eq. 31d)

Figure 5:
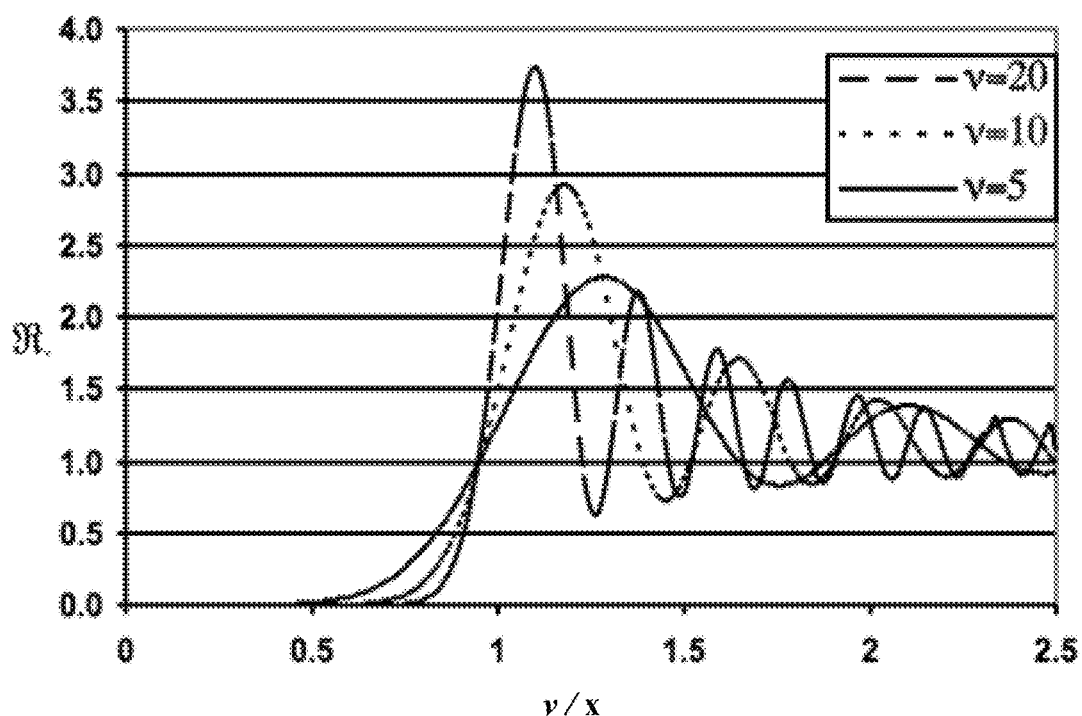
FIG. 5 shows a plot of the change in energy density from a mouth of a cavity mode, according to one embodiment.

$F = \int^{y_{nm}} J_m^2 y \, dy / I_{nm} = 1$ (Eq. 31e)

Where energy density of a given mode at the mouth of cavity is known, the change in energy density from the mouth of the cavity is contained within $\mathcal{R}\upsilon_\upsilon(x)$. Thus for a standing wave X=J with perfect reflection from the cavity, the energy density function is as shown in FIG. 5.

In any of the embodiments described above, the broadband oscillator may produce a range of wavelengths (e.g., broadband quantum cascade laser), as opposed to a single-frequency laser. In preferred embodiments, the broadband oscillator may further reduce energy usage by including the ability to limit the range of frequencies produced that correspond to a desired detection range.

Figure 6:
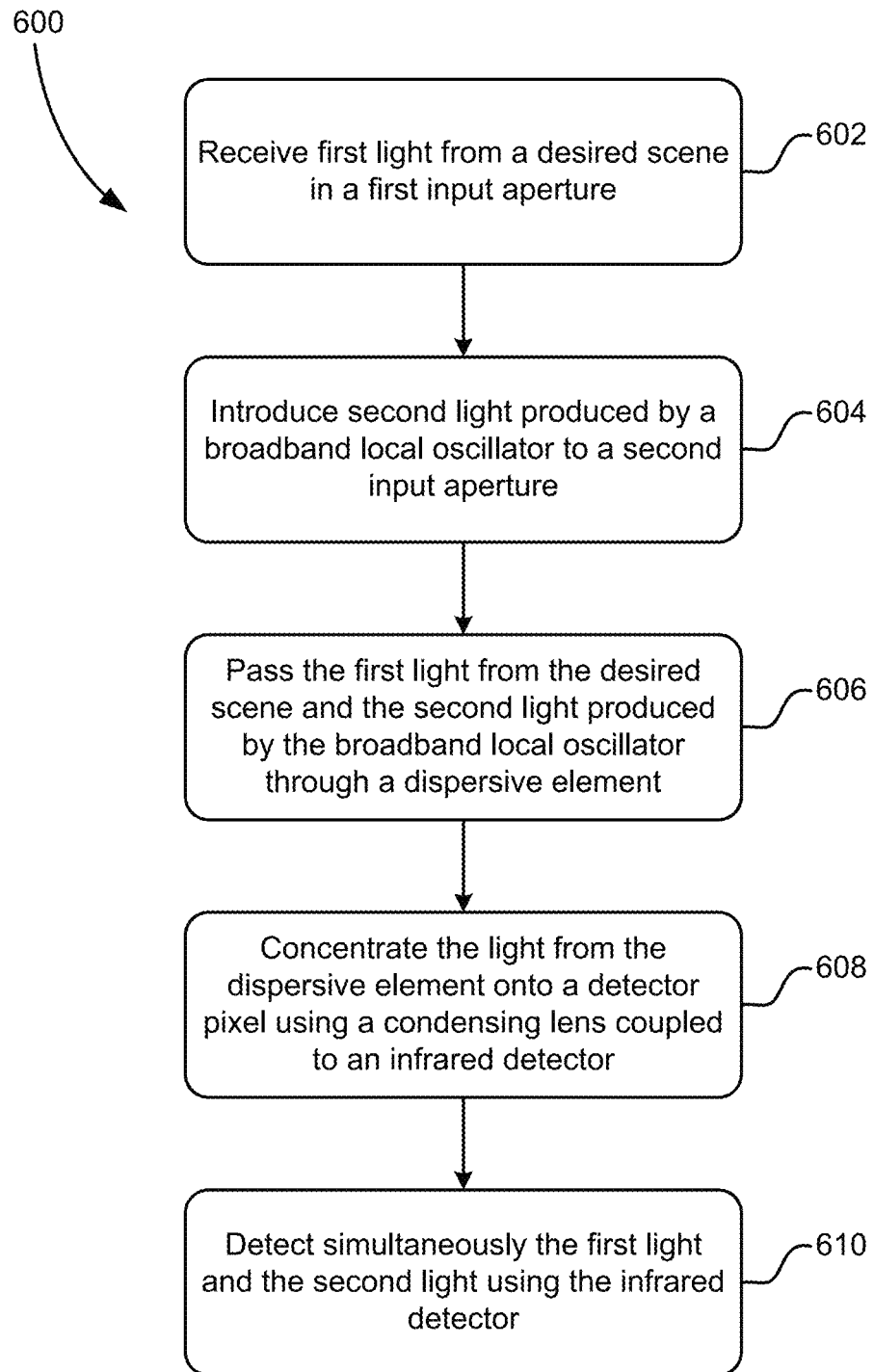
FIG. 6 is a flow diagram of a method for detecting light according to one embodiment.

Now referring to FIG. 6, a method 600 for detecting light is shown according to one embodiment. The method 600 may be carried out in any desired environment, including those shown in FIGS. 1 and 3, among others. Of course, the method 600 may include more or less operations than those shown in FIG. 6, as would be apparent to one of skill in the art upon reading the present descriptions.

In operation 602, first light is received from a desired scene in a first input aperture.

In operation 604, second light produced by a broadband local oscillator is introduced to a second input aperture. In one embodiment, the local broadband oscillator may include a broadband quantum cascade laser having broad spectral bands between about 500 cm$^{-1}$ and about 5000 cm$^{-1}$.

In one embodiment, the second light from the broadband local oscillator may be limited to a frequency that corresponds to a desired detection range, which may reduce power usage of the broadband local oscillator.

In one preferred approach, the first input aperture may be spatially offset from the second input aperture. The spatial offset may be based on a desired frequency and/or wavelength detection range, in some approaches.

In operation 606, the first light from the desired scene and the second light produced by the broadband local oscillator is passed through a dispersive element.

In operation 608, the light from the dispersive element is concentrated onto a detector pixel using a condensing lens coupled to the detector. In one embodiment, the condensing lens may include a plasmonic IR condensing lens, as previously described.

According to some approaches, the plasmonic IR condensing lens may have a conical shape tapering inward toward the sensor, and may include a Si core (or any other material as known in the art that is compatible with the light being concentrated) having a conductive metal cladding on radial surfaces thereof. The conductive metal cladding may be any material which operates to concentrate the light within the plasmonic lens, as known in the art, such as Au, Ag, Cu, etc. The conductive metal cladding may also be selected based on a gain provided by the conductive metal cladding, in more approaches.

In one embodiment, an angle measured from perpendicular to a planar surface of the sensor and a sidewall of the conical shape may be between about 5° and about 12°, for example about 8.5°.

According to another embodiment, the conical shape may have a first diameter at a distal end adjacent the detector of less than about one-half wavelength of incident light in Si. Also, the conical shape may have a second diameter at an end receiving the incident light from the dispersive element of approximately a diffraction limit set by the primary condensing lens. Of course, the dimensions may be chosen to increase the likelihood of light being concentrated by the plasmonic lens, according to techniques that would be apparent to one of skill in the art upon reading the present descriptions.

In operation 610, the first light and the second light are simultaneously detected using the detector. In one approach, the detector may include an array of photodetectors, as previously described.

In one preferred approach, the array of photodetectors may be sufficient in number to detect a desired frequency range with a desired resolution, in order to conserve energy usage of the array of photodetectors, among other advantages.

According to one embodiment, a frequency of the first light and a frequency of the second light may coincide at each pixel of the detector with a bandwidth determined by a spectral resolution of a spectrometer.

In an optional operation, a coherent beat frequency may be created using the two frequencies, wherein each area of the first and second input apertures times a collection solid angle of the spectrometer is about a wavelength squared (about $\lambda^2$).

While various embodiments have been described above, it should be understood that they have been presented by way of example only, and not limitation. Thus, the breadth and scope of a preferred embodiment should not be limited by any of the above-described exemplary embodiments, but should be defined only in accordance with the following claims and their equivalents.

What is claimed is:

1. A method of forming a plasmonic condensing lens for room temperature quantum noise limited (QNL) infrared (IR) spectrometry, the method comprising:
    forming a silicon cone on a substrate;
    coating the silicon cone with a highly reflective material; and
    modifying the silicon cone using focused ion beam (FIB) modification to permit transmittance of light through the silicon cone.

2. The method as recited in claim 1, wherein forming the silicon cone on the substrate comprises reactive ion etching.

3. The method as recited in claim 1, wherein the highly reflective material is selected from a group consisting of Au, Ag, Pt and Cu.

4. The method as recited in claim 1, wherein the substrate comprises $SiO_2$.

5. The method as recited in claim 1, wherein modifying the silicon cone using FIB produces a silicon cone characterized by an aperture diameter approximately one-seventh (1/7) that of a wavelength of light that is to be detected by a detector coupled to the silicon cone.

6. The method as recited in claim 5, wherein the detector is placed in direct contact with the aperture of the silicon cone.

7. The method as recited in claim 1, wherein the silicon cone is formed to have dimensions including a length of about 10 μm, a diameter at a receiving end of about 3.5 μm, and a diameter at a transmitting end of about 0.5 μm.

8. The method as recited in claim 1, comprising installing the plasmonic condensing lens in a heterodyne detection system for detecting light, the system comprising:
    a first input aperture configured to receive first light from a scene input;
    a second input aperture configured to receive second light from a local oscillator input;
    a broadband local oscillator configured to provide the second light to the second input aperture;
    a dispersive element configured to disperse the first light and the second light; and
    the plasmonic condensing lens coupled to an infrared detector,
    wherein the plasmonic condensing lens is configured to concentrate incident light from a primary condensing lens onto the infrared detector,
    wherein the infrared detector is a square-law detector configured to sense a frequency difference between the first light and the second light; and
    wherein each area of the first and second input apertures times an input collection solid angle of the system is about a wavelength squared (about $\lambda^2$).

9. The method as recited in claim 1, comprising installing the plasmonic condensing lens in a heterodyne detection system for detecting light, the system comprising:
    a first input aperture configured to receive first light from a scene input;
    a second input aperture configured to receive second light from a local oscillator input;
    a broadband local oscillator configured to provide the second light to the second input aperture;
    a dispersive element configured to disperse the first light and the second light; and
    the plasmonic condensing lens coupled to an infrared detector;

wherein the plasmonic condensing lens is configured to concentrate incident light from a primary condensing lens onto the infrared detector;

wherein the infrared detector is a square-law detector configured to sense a frequency difference between the first light and the second light;

wherein the plasmonic condensing lens has a conical shape tapering inward toward the infrared detector; and wherein the conical shape has a first diameter at an end adjacent the infrared detector of less than about one-half wavelength of the incident light in Si, and wherein the conical shape has a second diameter at an end receiving the incident light from the dispersive element of approximately a diffraction limit set by the primary condensing lens.

10. The method as recited in claim 1, comprising installing the plasmonic condensing lens in a heterodyne detection system for detecting light, the system comprising:

a first input aperture configured to receive first light from a scene input;

a second input aperture configured to receive second light from a local oscillator input;

a broadband local oscillator configured to provide the second light to the second input aperture;

a dispersive element configured to disperse the first light and the second light; and the plasmonic condensing lens coupled to a detector;

wherein the plasmonic condensing lens is configured to concentrate incident light from a primary condensing lens onto the detector; and wherein the detector is detector configured to sense a frequency difference between the first light and the second light.

* * * * *